United States Patent [19]

Blakeley et al.

[11] Patent Number: 4,694,837
[45] Date of Patent: Sep. 22, 1987

[54] CARDIAC AND RESPIRATORY GATED MAGNETIC RESONANCE IMAGING

[75] Inventors: Douglas M. Blakeley, Euclid; Carolyn A. Kershaw, Mentor; Raymond E. Gangarosa, Euclid, all of Ohio

[73] Assignee: Picker International, Inc., Highland Hts., Ohio

[21] Appl. No.: 764,440
[22] Filed: Aug. 9, 1985
[51] Int. Cl.[4] .................................................. A61B 5/05
[52] U.S. Cl. ................................... 128/653; 128/671; 128/696
[58] Field of Search ............... 128/653, 696, 706, 671, 128/723, 700, 736; 455/612, 613; 324/306, 309

[56] References Cited

U.S. PATENT DOCUMENTS

| | | | |
|---|---|---|---|
| 3,587,562 | 6/1971 | Williams | 128/671 |
| 3,795,247 | 3/1974 | Thaler | 128/419 P |
| 3,818,900 | 6/1974 | Nickel | 128/671 |
| 3,871,360 | 3/1975 | Van Horn et al. | 128/671 |
| 3,910,257 | 10/1975 | Fletcher et al. | 128/670 |
| 3,954,098 | 5/1976 | Dick et al. | 128/661 |
| 3,993,995 | 11/1976 | Kaplan et al. | 128/2 R |
| 4,070,572 | 1/1978 | Summerhayes | 250/199 |
| 4,079,730 | 3/1978 | Wikswo et al. | 128/2.05 F |
| 4,161,651 | 7/1979 | Sano et al. | 250/199 |
| 4,182,311 | 1/1980 | Seppi et al. | 128/653 |
| 4,245,507 | 1/1981 | Samulski | 128/736 |
| 4,303,077 | 12/1981 | Lewin et al. | 128/777 |
| 4,319,186 | 3/1982 | Kingsley | 324/96 |
| 4,382,184 | 5/1983 | Wernikoff | 128/653 X |
| 4,387,722 | 6/1983 | Kearns et al. | 128/716 |
| 4,409,550 | 10/1983 | Fossel et al. | 324/300 |
| 4,413,233 | 11/1983 | Fossel et al. | 324/300 |
| 4,442,350 | 4/1984 | Rashleigh | 250/227 |
| 4,473,841 | 9/1984 | Murakoshi et al. | 455/612 |
| 4,506,678 | 3/1985 | Russell et al. | 128/696 |
| 4,523,099 | 6/1985 | Lavine | 455/612 |
| 4,545,384 | 10/1985 | Kawachi | 128/653 |
| 4,547,892 | 10/1985 | Richey et al. | 128/653 |
| 4,564,017 | 1/1986 | Glover | 128/653 |
| 4,607,223 | 8/1986 | Mallard | 324/309 |
| 4,626,110 | 12/1986 | Wickersheim et al. | 128/736 |

FOREIGN PATENT DOCUMENTS

| | | |
|---|---|---|
| 0096487 | 12/1983 | European Pat. Off. . |
| 0117725 | 9/1984 | European Pat. Off. . |
| 0132785 | 2/1985 | European Pat. Off. . |
| 2854774 | 10/1980 | Fed. Rep. of Germany . |
| 2273505 | 2/1976 | France .................... 128/671 |
| 2027208 | 8/1978 | United Kingdom . |

OTHER PUBLICATIONS

"Cardiac Responsibility to Pulsed Magnetic Fields with Regard to Safety in NMR Imaging", by McRobbie et al., Phys. Med. Biol., 1985, vol. 30, No. 7, pp. 695-702.
"Magnetic Resonance Imaging with Respiratory Gating", by Ehman et al., AJR 143, Dec. 1984, pp. 1175-1182.
"Respiratory Gating in Magnetic Resonance Imaging at 0.5 Tesla", by Runge et al., Radiology, 1984, 151; 521-523.
Dynamic Measurements Corp., product literature for System 5610 Fiber-Optic Data Link.

*Primary Examiner*—Kyle L. Howell
*Assistant Examiner*—Ruth S. Smith
*Attorney, Agent, or Firm*—Fay, Sharpe, Beall, Fagan, Minnich & McKee

[57] ABSTRACT

A magnetic resonance imaging apparatus (A) generates a uniform main magnetic field, gradient fields transversely thereacross, excites resonance in nuclei within an image region, receives radio frequency signals from the resonating nuclei, and reconstructs images representative thereof. Electrodes (30) monitor the cardiac cycle of a patient (B) being imaged and an expansible belt (32) monitors the respiratory cycle. A carrier signal from a generator (52) is modulated with the respiratory signals. The modulated carrier signals are combined (60) with the cardiac signals and converted to a light signal by a light source (62). A fiber optic cable (36) conducts the light signals to a light receiver (70). Band pass filters (72, 100) separate the received cardiac and respiratory encoded carrier signals. A zero detector (80) provides a scan initiation signal in response to a preselected portion of the cardiac cycle. The respiratory encoded carrier signal is demodulated by demodulator (102) and a comparator (116) blocks or enables the processing of image data during a selected window of the respiratory cycle. A window adjustment means (118) adjusts the respiratory window as a function of phase encoding of the resonating nuclei.

20 Claims, 3 Drawing Figures

CARDIAC AND RESPIRATORY GATED MAGNETIC RESONANCE IMAGING

BACKGROUND OF THE INVENTION

The present invention relates to the electronic, anatomical examination arts. More particularly, it relates to the gating and control patient imaging in conjunction with body motion of the patient. Particular application is found in conjunction with cardiac and respiratory gating of magnetic resonance imaging and the invention will be described with particular reference thereto. However, it is to be appreciated that the invention may have other application in other electronic imaging fields and in conjunction with monitoring other anatomical motion.

Heretofor, magnetic resonance images have commonly been constructed from about 256 views, each view requiring about 200-1000 milliseconds to acquire. When imaging through the patient's chest or abdomen, the images tend to become blurred or degraded by cardiac and respiratory motion.

Various cardiac and respiratory monitors have been utilized in computerized tomography and other imaging systems. For sensing cardiac function, conductive wires or leads commonly carried cardiac signals from the patient area adjacent the imaging zone to a remotely located signal processing circuit. In magnetic resonance imaging, conducting leads extending into the imaging zone cause significant degradation of the acquired image. The degradation is a result of penetration of the RF barrier by conducting wire which conveys RF noise present in the atmosphere into the imaging area. In all patient monitoring devices, high current and voltage isolation devices are necessary to protect the patients from hazardous shocks. Fiber optic conductors, for example, convey sensed cardiac monitor signals without the risk of patient shock and maintain the RF integrity of the imaging system.

In magnetic resonance imaging apparatus, relatively strong gradient magnetic fields are applied during acquisition of each view. These changing magnetic fields induce stray currents in electronic circuitry associated with cardiac monitoring adjacent the imaging zone. These induced currents tend to interfere with the cardiac monitoring function and signals indicative thereof. In particular, the changing gradient fields tend to generate signals which are similar in appearance to the signals which represent a cardiac R-wave in the cardiac electrocardiogram (ECG) cycle. Because many cardiac monitors key on the R-wave portion, these gradient magnetic field changes tend to produce false cardiac signals.

The present invention contemplates a new and improved anatomical gating system which overcomes the above referenced problems and others.

SUMMARY OF THE INVENTION

In accordance with a first aspect of the present invention, an anatomical condition responsive gating apparatus is provided for magnetic resonance and other imagers. A first anatomical condition detector monitors a first anatomical condition, e.g. occurance of a preselected portion of the cardiac cycle, of a patient to be imaged. A second anatomical condition detector detects a second anatomical condition, e.g. an occurance of a preselected chest expansion, of the patient to be imaged. A light source produces a light signal which is encoded in accordance with both the first and second anatomical conditions as monitored by the first and second antomical condition detectors. A light signal receiver receives the encoded light signal from the light source. A scan triggering means enables the initiation of an imaging scan in response to receipt of a light signal encoded in accordance with the first anatomical condition. A scan blocking means prevents processing of magnetic resonance imaging data in response to receipt of light signals encoded in accordance with the second anatomical condition. The scan triggering and blocking means are operatively connected with the light signal receiver.

In accordance with a more limited aspect of the present invention, a magnetic resonance imaging apparatus is provided in combination with the anatomical condition response gating apparatus.

In accordance with another aspect of the present invention, a cardiac and respiratory gating apparatus is provided. a cardiac cycle detector monitors the cardiac cycle of the patient and produces a cardiac signal indicative thereof. A respiratory cycle detector monitors the respiratory movement of the patient and produces a respiratory signal indicative thereof. A signal modulating means encodes a carrier signal with one of the cardiac and respiratory signals to produce a modulated carrier signal. A signal combining means combines the modulated carrier signal with the other of the cardiac and respiratory electrical signals to produce a combined signal. A light source converts the combined signal into an encoded light signal which is conveyed by a fiber optic light guide to a light signal receiver. A carrier signal separating means separates the modulated carrier signal from other received signals. A demodulator demodulates the encoded carrier signals such that separate cardiac and respiratory signals are recovered.

In accordance with yet another aspect of the present invention, a method of gating magnetic resonance imaging is provided. First and second anatomical conditions are monitored. A light signal is produced which is encoded in accordance with both the first and second monitored anatomical conditions. The encoded light signal is received and signals indicative of the first and second anatomical conditions are separated therefrom. A magnetic resonance imaging scan is initiated in resposne to the occurance of a selected event in the received first anatomical condition signal. The processing of magnetic resonance imaging data is selectively prevented and permitted in accordance the received second anatomical condition signal.

One advantage of the present invention is that it provides a non-conducting link between patient monitoring equipment adjacent the imaging region and other electrical progressing circuitry.

Another advantage of the present invention is that it eliminates and suppresses electrical interference which is caused by magnetic fields and field changes during magnetic resonance imaging.

Another advantage of the present invention is that multiple monitored anatomical condition signals are conveyed on a signal data transmission link without poling or central synchronization.

Yet another advantage of the present invention is that is separates cardiac signals and interference signals attributable to changing magnetic gradient fields.

Still further advantages of the present invention will become apparent to those of ordinary skill in the art upon reading and understanding the following detailed description of the preferred embodiment.

BRIEF DESCRIPTION OF THE DRAWINGS

The present invention may take form in various parts and arrangements of parts or in various steps and arrangements of steps. The drawings and pictured components are only for purposes of illustrating a preferred embodiment and are not to be construed as limiting the invention.

DETAILED DESCRIPTION OF THE PREFERRED EMBODIMENT

Figure 1:
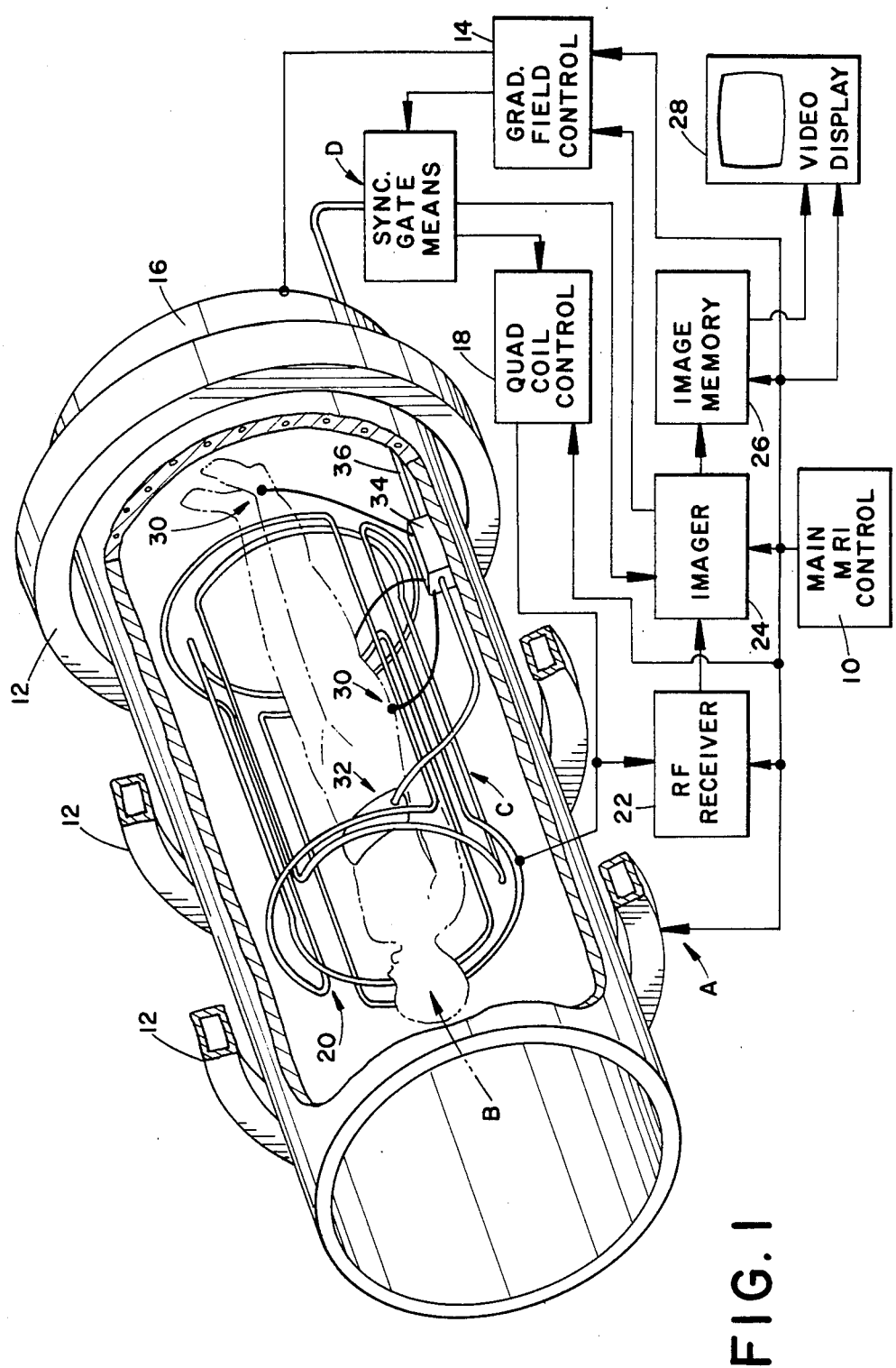
FIG. 1 is a diagrametic illustration of a magnetic resonance imaging apparatus incorporating the present invention.

With reference to FIG. 1, a magnetic resonance imaging apparatus A receives a patient B of whom an image is to be generated. An anatomical monitoring means C is disposed adjacent the patient within the magnetic resonance imaging apparatus to monitor anatomical conditions of the patient. A synchronizing means D receives optically encoded signals from the anatomical monitoring means C and gates the magnetic resonance imaging apparatus A in accordance therewith.

The magnetic resonance imaging apparatus A includes main MRI controller 10 which directs each of the following subsystems. A main magnet 12 generates a strong, uniform magnetic field longitudinally along the image region. A gradient field control 14 causes a gradient coil 16 to generate magnetic field gradients in the image region at selected angular orientations. A quadrature coil control means 18 causes quadrature coils 20 to excite magnetic resonance of selected nuclei in the image region and to receive radio frequency resonance signals therefrom. Received radio frequency resonance signals are conditioned by a radio frequency receiver 22 and processed by an imager 24 to produce data indicative of an image of a selected region of the patient. The image data are stored and accumulated in an image memory 26. A display means 28, such as a video monitor, produces a man-readably display of the imaged data.

The patient monitor means C includes a first anatomical condition detector, in the preferred embodiment electrodes 30 for monitoring the patient's electrocardiogram cycle. The electrodes are attached to the patient in a known manner. A second anatomical conditiondetector monitors a second anatomical condition of the patient; particularly, a respiratory cycle monitoring means 32 monitors the patient's respiratory cycle. In the preferred embodiment, the respiratory monitor is an air filled elastomeric belt which expands and contracts with the patient's breathing. The expansion and contraction causes corresponding changes in the air pressure that are converted to electrical signals which are indicative of the patient's respiratory cycle.

Figure 2:
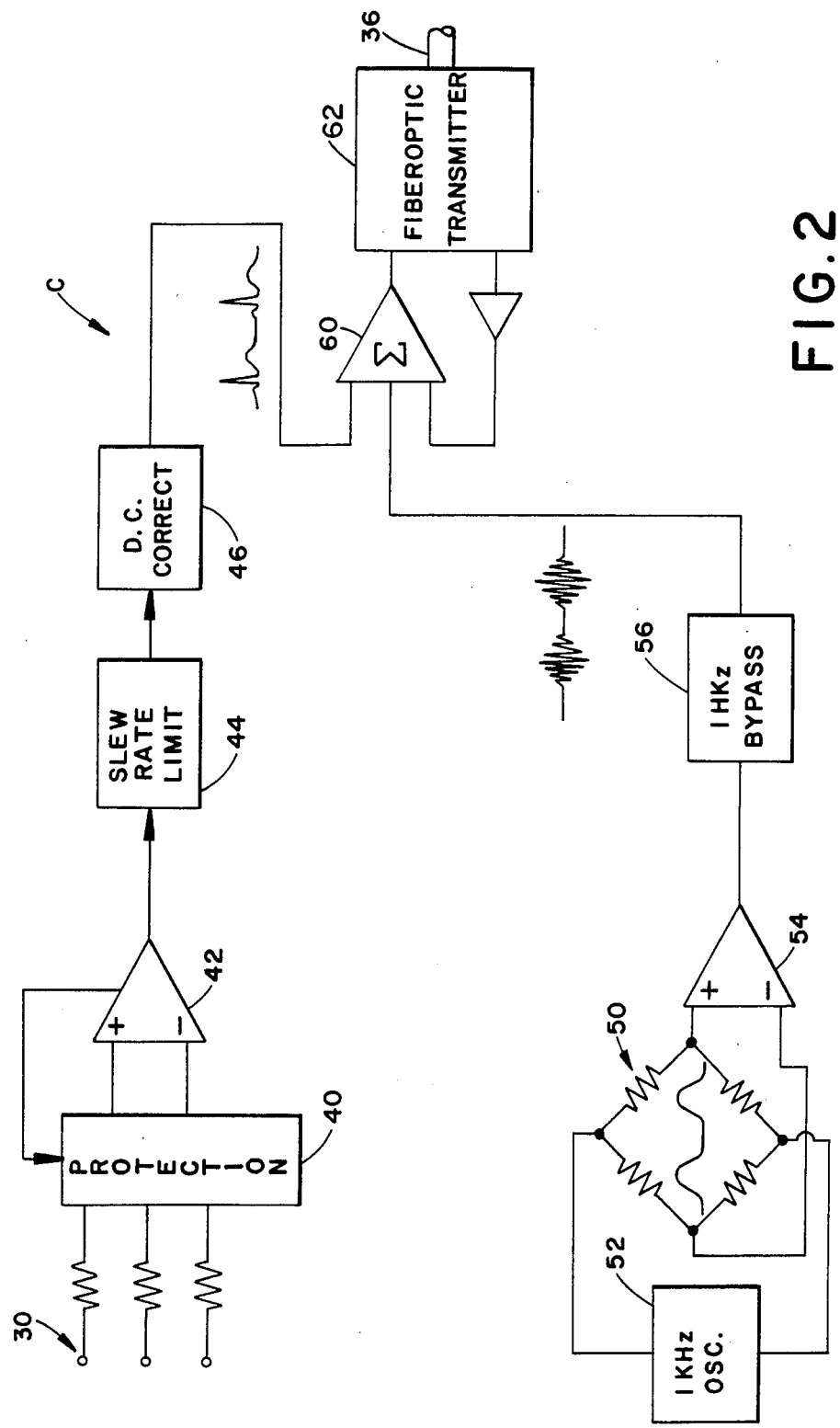
FIG. 2 is a circuit diagram of a patient monitoring and light signal transmitting portion of the present invention; and, FIG. 3 is a circuit diagram of a light signal processing and magnetic resonance imager controlling portion of the present invention.

A patient monitor circuit 34, which is illustrated in greater detail in FIG. 2, amplifiers the monitored cardiac and respiratory cycle data and produces a light signal which is encoded in accordance with both the monitored cardiac and respiratory conditions. The patient monitor circuit 34 is disposed adjacent the patient and within the magnetic field. A light pipe or optic fiber wave guide 36 conveys the cardiac, respiratory, or other anatomical data from the high magnetic field region. Optionally, infrared telemetry may be used.

The gating means D causes the quadrature coil control means 18 to initiate a magnetic resonance view a preselected duration after each R-wave peak of the electrocardiogram cycle. The duration after the R-wave peak is selected to permit imaging at a selected portion of the cardiac cycle. The gating means further blocks the processing of data from the portions of the respiratory cycle in which respiratory movement is grestest. The processing of data is enabled during the most quiescent portions of the respiratory cycle. The blocking and enabling of data processing may be achieved by enabling and disabling operation of the quadrature coil control means 18, by enabling and disabling the imager 24, or controlling other control functions from the main magnetic resonance imaging controller 10.

The gradient field controller 14 is connected with the gating means D to prevent the initiation of a scan while the gradient field is being applied. Normally, of course, the main magnetic resonance imaging controller 10 would not cause a scan to be initiated at this point. However, the gradient field may cause generation of noise signals which are confusingly similar to electrocardiogram R-wave signals. Blocking initiation of a scan while the gradient field is applied prevents the moving gradient field related noise from inappropriately triggering a scan.

With reference to FIG. 2, the cardiac monitoring electrodes 30 are connected with a protection circuit 40 which protects the electronics in the unlikely event of defibrillation of patient and removes RF signals sensed by the monitoring electrodes. An amplifier 42 adjusts the magnitude of the first anatomical condition or cardiac signals. A slew rate limiting circuit 44 and a DC correction circuit 46 minimizes distortions in the cardiac signal caused by the magnetic gradients and removes DC offset present on most electrocardiograms.

The respiratory sensing belt is connected with a balanced bridge type pressure transducer 50 which produces an electrical signal that varies in amplitude with the respiratory cycle. Commonly, the cardiac cycle is about one second in length and the respiratory cycle is about five to ten seconds in length. Because the cardiac and respiratory cycles are of such similar frequency, there is a tendency for the two signals, if mixed, to become inseparable. To overcome this problem, an audio frequency carrier signal generator 52 applies an audio frequency carrier signal, e.g. one kilhertz, across the balanced bridge pressure transducer. This modulates or encodes the carrier signal in accordance with the second anatomical condition, i.e. the monitored pressure. A beat pattern or amplitude variation carries the encoded respiratory cycle data. In the preferred embodiment, the carrier signal is amplitude modulated. Optionally, frequency modulation or other encoding techniques may be utilized. An amplifier 54 increases the amplitude of the encoded carrier signal. A band pass filter 56 removes distortion and superimposed off frequency signal components.

A signal combining or summing means 60 adds or otherwise combines the cardiac and respiratory signals. A fiber optic transmitter 62, which includes a light source for generating a light and an encoding means for encoding the light in accordance with the cardiac and respiratory encoded data. In the preferred embodiment, the frequency of the light signal from the light source is modulated in proportion to the magnitude of the voltage of the combined cardiac and respiratory signals from the signal combining means 60.

Figure 3:
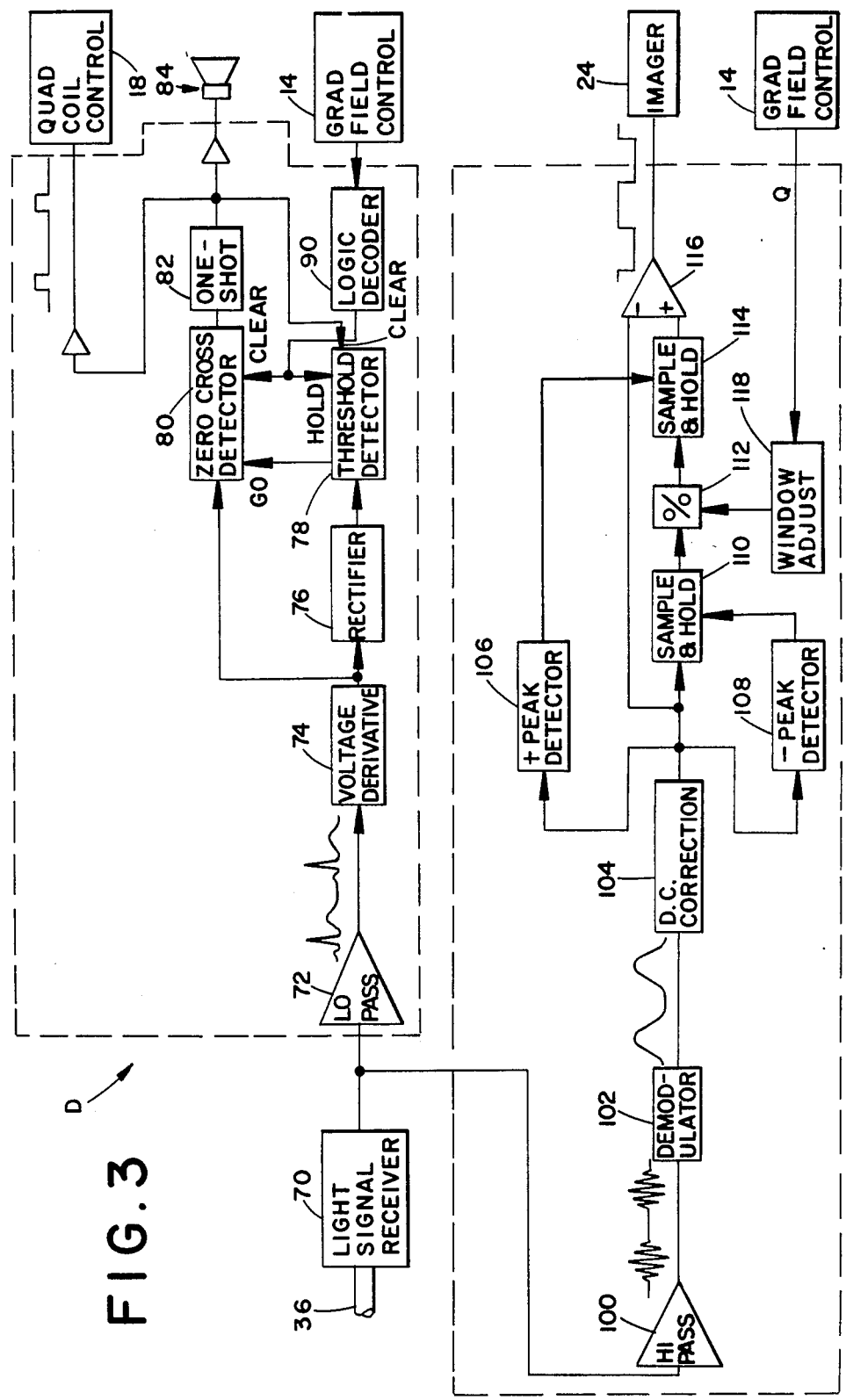

With particular reference to FIG. 3, a light signal receiver 70 receives the light signal from the fiber optic cable 36 and produces a corresponding received, combined data signal. A received signal separating means includes a low pass filter 72 for passing only signal components with the frequency on the order of the cardiac signal, i.e. separates the cardiac component of the received signal from other components. A 50 to 200 hertz low pass filter is preferred for separating cardiac data. Optionally, when monitoring other anatomical conditions, other signal separating menas may be utilized.

A voltage derivative means 74 removes and DC offset introduced by the fiber optic link 36 and produces a voltage proportional to the change in voltage per unit time of the electrocardiogram signal. A rectifying means 76 rectifies the signal to produce a signal of the proper polarity for a threshold detector 78 to detect R-wave peaks of the cardiac cycle. The threshold detector 78 establishes a threshold level at two thirds of the previous R-wave peak derivative. Once the threshold has been exceeded a zero cross means 80 searches for the next occurence of zero crossing of the derivative signal. Comparing the derivative of the received cardiac signal with two thirds of the previous R-wave peak derivative locates the R-wave peak of the current cardiac signal In this manner, variations in the derivative of the cardiac signals are automatically corrected.

A one shot multi-vibrator 82 generates a square wave trigger pulse of approximately 150 milliseconds in response to each R-wave peak. An audible indicator 84 provides an audible indication of each heart beat from the R-wave trigger pulse. The leading edge of each 150 millisecond trigger pulse is conveyed to the quadrature coil control means 18 to initiate the next scan.

The gradient field controller 14 produces a blanking signal as the gradient magnetic field is being applied. A blanking means blocks the initiation of the magnetic resonance imaging scan during application of the magnetic field gradient. In particular, a logic decoder 90 receives and blanks or otherwise prevents the threshold detector 78 from adjusting the threshold level and the zero-cross detector 80 from initiating a scan.

The signal separating means further includes a respiratory or second anatomical condition separating means 100, such as a 700 hertz high pass filter, for separating the respiratory signal component from the cardiac and other components. A demodulator 102 demodulates the encoded carrier signal to produce a voltage which varies with the respiratory cycle. A DC correction means 104 establishes a zero level for subsequent peak detection.

A positive peak detector 106 and a negative peak detector 108 search for the respective extremes of the respiratory signal cycle. A first respiratory extreme, particularly the negative peak magnitude, is stored in a first or negative sample and hold circuit 110. A multiplier means 112 reduces the stored peak amplitude a preselected percentage, e.g. 70%. A second sample and hold circuit 114 stores the preselected percentage of the previous negative peak magnitude when enabled by the positive peak detector 106. This establishes a threshold for detecting the next rest period of the respiratory cycle.

A comparing means 116 compares the present respiratory signal amplitude with the threshold or window established in the second sample and hold 114. When the signal is less than the threshold, an enable or high signal is produced which allows scan data to be accepted and processed by the imager 24. When the received respiratory signal is greater than the threshold level, a blocking or data discard signal is generated which blocks the imager from accepting imaged data. This enable/blocking or window signal provides a window within which the received data may be processed.

Preferably, the window is slidably adjustable in order to optimize scan times. That is, limited amounts of data at the begining of chest expansion and at the end of chest contraction may be processed with minimal degradation to the resultant image. At the beginning and ending of respiratory motion, the patient's chest is substantially at the quiescent stage. Rather than discarding any data in which the window signal is low during any portion of the scan data acquisition, the data may be retained if the signal remains low or turns low for only a small portion of the data receiving period. In some applications, it may be desirable to accelerate image data collection at the prince of incorporating data scans collected during the limited respiratory movement. To this end, the window is selectively adjustable to permit either only data collected during the quiescent portions of the respiratory cycle or data collected in both quiescent and less quiescent portions of the respiratory cycle to be incorporated into the image.

In the preferred embodiment, the window is dynamically variable in accordance with the phase encoding the view being acquired. Views with smaller phase angle encoding have a greater effect on the final image quality than views with higher phase angle encoding. The motion requirements are relaxed for the less sensitive, greater phase angle encoded views relative to the smaller phase angle encoded views.

A window adjusting means 118 selectively and dynamically increases the decreases the window as a function of the angle of phase encoding. For example, the multiplier means 112 may multiply the stored peak value by one of three preselected percentages depending upon whether the current view has smaller, greater, or intermediate phase encoding. Optionally, the window may be increased or decreased along a continuum in other increments, as other functions of the phase angle, or the like.

The dynamically varying window is of particular advantage in multi-slice data acquisition. The body's position is more likely to change between the collection of the first and last slice than during the acquisition of a single slice view. The dynamic window variation reduces the examination time by requiring little respiratory motion for smaller phase angle multi-slice views and relaxing the respiratory motion requirements as the phase angle increases.

Optionally, the window adjustment may also account for the breathing patterns of the patient. In particular, patients with long respiratory cycle repeat times are more likely to produce data which falls entirely during a quiescent period of the respiratory cycle than a patient with a shorter respiratory cycle. For a patient with a short respiratory cycle, a less stringent window quality may be necessary to produce an image in an acceptable duration of time.

The invention has been described with reference to the preferred embodiment. Obviously, modifications and alterations will occur to others upon reading and understanding the preceding specification. It is intended that the invention be construed as including all such alterations and modifications in so far as they come within the scope of the appended claims or the equivalents thereof.

Having thus described the preferred embodiment, the invention is now claimed to be:

1. An anatomical condition gating apparatus for a magnetic resonance imager, the apparatus comprising:

a first anatomical condition detector means for monitoring at a first anatomical site within an imaging magnetic field of the imager a first anatomical condition of a patient to be imaged;

a second anatomical condition detector means for monitoring at a second anatomical site within the imaging magnetic field a second anatomical condition of the patient to be imaged;

a light source means for transmitting a light signal from within the imaging magnetic field to a light signal receiver disposed out of the imaging magnetic field;

an encoding means for encoding the light signal within the imaging magnetic field in accordance with both the first and second anatomical conditions monitored by the first and second anatomical condition detector means, the encoding means being operatively connected with the first and second anatomical condition detector means and the light source means, whereby information about the first and second monitored anatomical conditions is transmitted through the imaging magnetic field without altering the imaging magnetic field;

a light signal decoding means operatively connected with the light signal receiver for recovering first and second anatomical condition encodings from the encoded light signal;

a scan triggering means for initiating imaging scans in accordance with the first anatomical condition encoding of the received light signal, the scan triggering means being operatively connected with the light signal decoding means; and, a scan blocking means for preventing processing of imaging data in accordance with the second anatomical condition encoding of the received light signal, the scan blocking means being operatively connected with the light signal decoding means.

2. The gating apparatus as set forth in claim 1 wherein the imaging magnetic field includes a series of magnetic field gradient pulses and further including blanking means for preventing initiation of imaging scans during an application of one of the magnetic field gradient pulses.

3. The gating apparatus as set forth in claim 1 further including carrier signal means for generating a carrier signal that oscillates with a carrier frequency which carrier signal is encoded in accordance with the second type of anatomical condition, the carrier signal means being operatively connected between the second anatomical condition detector means and the encoding means.

4. The gating apparatus as set forth in claim 3 wherein the decoding means includes a carrier frequency separating means for separating the encoded carrier frequency signal from other received signals, the carrier frequency separating means being operatively connected between the light signal receiver and at least one of the scan triggering and blocking means.

5. The gating apparatus as set forth in claim 1 further including a fiber optic cable for conducting light between the light source means and the light signal receiver.

6. The gating apparatus as set forth in claim 1 further including a window adjusting means for selectively adjusting the blocking means to adjust a relationship between the second anatomical condition and the preventing of image data processing.

7. A magnetic resonance imaging apparatus in which imaging is gated in response to anatomical conditions of an imaged patient, the apparatus comprising:

a main magnetic field generating means for generating a main magnetic field substantially uniformly and longitudinally through a patient imaging region;

a gradient field means for generating magnetic field gradients across the main magnetic field with phase encodings at a plurality of phase angles;

an excitation means for causing selective resonance of nuclei within the image region;

a receiving means for receiving resonance signals generated by the resonating nuclei;

an image reconstruction means for reconstructing an image representative of the resonating nuclei in the image region from the received resonance signals, the image reconstruction means being operatively connected with the receiving means;

a first anatomical condition detector means for producing a first condition signals which varies in accordance with a first monitored anatomical condition of the patient, the first anatomical condition detector means being disposed adjacent the image region;

a second antomatical condition detector means for producing a second condition signal which varies in accordance with a second monitored anatomical condition of the patient, the second anatomical condition detector means being disposed adjacent the image region;

a signal source means for propagating a signal to a remote location, without generating magnetic fields adjacent the image region, whereby first and second anatomical condition information is conveyed through the main magnetic field adjacent the image region without generating magnetic fields that would have distorted the main and gradient magnetic fields;

an encoding means for encoding the signal in accordance with the first and second anatomical condition signals, the encoding means being operatively connected with the first and second anatomical condition detectors and the source means and being disposed within the main magnetic field adjacent the image region;

a signal receiver means for receiving the encoded signal, the signal receiver means being operatively connected with the source means at the remote location;

a scan triggering means for initiating a magnetic resonance imaging scan in response to the first anatomical condition encoding of the signal, the scan triggering means being operatively connected with the signal receiver means and at least one of the resonance excitation means and the image reconstruction means; and, a scan blocking means for preventing processing of the resonance signals in response to the second anatomical condition encoding of the received signal, the scan blocking means being operatively connected with the signal receiver means and the image reconstruction means, whereby the initiation of scans and the processing of data is coordinated with anatomical conditions of the patient.

8. The apparatus as set forth in claim 7 further including a blanking means for preventing initiation of magnetic resonance imaging scans during a change in the magnetic field gradient, the blanking means being operatively connected with the gradient field control means and with the scan triggering means.

9. The apparatus as set forth in claim 8 wherein the first anatomical condition detector means includes a first monitoring means for monitoring the patient's cardiac cycle such that the first condition signal is indicative of the patient's cardiac cycle and wherein the second anatomical condition detector means includes a second monitoring means for monitoring the patient's respiratory cycle such that the second condition signal is indicative of the patient's respiratory cycle, whereby imaging scans are initiated in response to a selected portion of the cardiac cycle and image reconstruction from resonance signals generated during selected portions of the respiratory cycle is prevented.

10. The apparatus as set forth in claim 9 further including a carrier signal means for generating a carrier signal having a carrier frequency and a carrier signal modulating means for modulating the carrier signal with one of the cardiac and respiratory signals.

11. The apparatus as set forth in claim 10 further including a signal combining means for combining the modulated carrier signal with the other of the cardiac and respiratory signals, the encoding means being operatively connected with the signal combining means such that the signal is encoded with both respiratory and cardiac information, one carried at its natural frequency and the other carried at the carrier frequency.

12. The apparatus as set forth in claim 11 further including a carrier frequency separating means for separating the modulated carrier signal from other signals and a demodulating means for removing the carrier frequency from the modulated carrier signal, one of the frequency separating means and the demodulating means being connected with the scan triggering means for conveying the cardiac signal thereto and the other being operatively connected with the scan blocking means for conveying the respiratory signal thereto.

13. The apparatus as set forth in claim 7, further including a fiber optic cable for conveying light between the signal source means and the signal receiver means.

14. The apparatus as set forth in claim 7 further including window adjusting means for selectively adjusting the blocking means.

15. A method of gating imaging in accordance with first and second anatomical conditions of an imaged patient, the method comprising:
   monitoring the first anatomical condition of the patient and generating a first electrical signal in accordance therewith;
   monitoring the second anatomical condition of the patient and generating a second electrical signal in accordance therewith;
   combining both the first and second electrical signals into a combined signal and encoding a light signal therewith;
   receiving the encoded light signal and generating a received electrical signal which is encoded in accordance with the first and second anatomical conditions;
   separating components of the received electrical signal which are indicative of the monitored first and second anatomical conditions;
   initiating collection of imaging data in response to the first anatomical condition indicative signal; and,
   selectively preventing processing of the imaging data in accordance with the second anatomical condition.

16. The method as set forth in claim 15 further including the steps of:
   generating a uniform main magnetic field encompassing a region of a patient to be imaged;
   periodically initiating a magnetic resonance imaging sequence which includes applying magnetic field gradients transversely across the main magnetic field in the image region, exciting magnetic resonance in the image region, and collecting magnetic resonance data; and,
   preventing the initiation of a magnetic resonance imaging sequence during application of the magnetic field gradients.

17. The method as set forth in claim 15 further including the steps of generating a carrier signal and modulating the carrier signal in accordance with one of the monitored first and second anatomical conditions such that in the combining step, the modulated carrier signal is combined with the other anatomical condition signal.

18. The method as set forth in claim 15 wherein the first anatomical conidition is the patient's cardiac cycle and the second anatomical condition is the patient's respiratory cycle.

19. The method as set forth in claim 15 further including the steps of:
   generating a uniform magnetic field encompassing a region of a patient to be imaged;
   exciting resonance of nuclei in the image region and generating a resonance signal which carries the imaging data;
   phase encoding the resonance signal with a plurality of phase angles;
   adjusting the relationship between the second anatomical condition and the preventing of image data processing in accordance with the encoded phase angle.

20. A magnetic resonance imaging apparatus in which imaging is gated in response to cardiac cycles of an imaged patient, the apparatus comprising:
   a main magnetic field generating means for generating a main magnetic field substantially uniformly and longitudinally through a patient imaging region;
   a cardiac monitor including lead wires leading from electrodes attached to the patient's skin to a cardiac signal producing means for producing cardiac signals which vary in accordance with the patient's cardiac cycles;
   a gradient field means for generating magnetic field gradient pulses across the main magnetic field, the magnetic field gradient pulses inducing electrical currents in the lead wires of the cardiac monitor, which induced currents cause the cardiac signal producing means to generate erroneous cardiac signals based on the induced currents;

an excitation means for causing selective resonance of nuclei within the image region;

receiving means for receiving resonance signals generated by the resonating nuclei;

an image reconstruction means for reconstructing an image representation of the resonating nuclei in the image region from the received resonance signals, the image reconstruction means being operatively connected with the receiving means;

a magnetic resonance imaging control means for controlling magnetic resonance imaging sequences including the application of magnetic field gradient pulses, the excitation of magnetic resonance, the receiving of magnetic resonance signals, and the reconstruction of an image representation from the received signals, the magnetic resonance imaging control means being operatively connected with the gradient field means, the excitation means, the receiving means, and the image reconstruction means;

a triggering means operatively connected with the cardiac signal producing means for initiating a magnetic resonance imaging sequence by the magnetic resonance imaging control means in response to a selected phase of the cardiac signal, whereby the magnetic resonance imaging scans are coordinated with the selected phase of the cardiac cycle; and, a blanking means operatively connected with the gradient field means and the magnetic resonance imaging control means for preventing the initation of imaging scans during an application of one of the magnetic field gradient pulses, whereby erroneous signals induced by the magnetic field gradient pulses are prevented from initiating an imaging scan.

* * * * *